United States Patent
Kim

(10) Patent No.: US 9,205,159 B2
(45) Date of Patent: Dec. 8, 2015

(54) MULTI-CHARGING AND STERILIZING APPARATUS

(71) Applicant: Seoul Viosys Co., Ltd., Ansan-si (KR)

(72) Inventor: Jong-Rak Kim, Seoul (KR)

(73) Assignee: SEOUL VIOSYS CO., LTD., Ansan-Si (KR)

( * ) Notice: Subject to any disclaimer, the term of this patent is extended or adjusted under 35 U.S.C. 154(b) by 0 days.

(21) Appl. No.: 14/530,481

(22) Filed: Oct. 31, 2014

(65) Prior Publication Data

US 2015/0115173 A1    Apr. 30, 2015

(30) Foreign Application Priority Data

Oct. 31, 2013 (KR) .................. 10-2013-0131223
Sep. 5, 2014 (KR) .................. 10-2014-0118851

(51) Int. Cl.
*A61L 2/10* (2006.01)
*A61L 2/00* (2006.01)
*B01J 19/08* (2006.01)
*B01J 19/12* (2006.01)
*A61N 5/06* (2006.01)
*A61N 2/10* (2006.01)
*H02J 7/00* (2006.01)

(52) U.S. Cl.
CPC ............. *A61L 2/10* (2013.01); *H02J 7/0013* (2013.01); *H02J 7/0045* (2013.01)

(58) Field of Classification Search
USPC ............. 250/372, 453.11, 454.11, 455.11, 250/458.1, 459.1, 461.1, 492.1, 492.2, 250/504 R, 504 H, 526; 422/1, 24, 29, 186, 422/186.3
See application file for complete search history.

(56) References Cited

U.S. PATENT DOCUMENTS

| | | | |
|---|---|---|---|
| 7,976,777 B2 * | 7/2011 | Gutman | 422/24 |
| 2006/0008400 A1 * | 1/2006 | Gutman | 422/292 |
| 2006/0158455 A1 * | 7/2006 | Yoshino | 345/589 |
| 2015/0137762 A1 * | 5/2015 | Kim et al. | 320/115 |

* cited by examiner

*Primary Examiner* — Bernard E Souw
(74) *Attorney, Agent, or Firm* — Perkins Coie LLP

(57) ABSTRACT

A multi-charging and sterilizing apparatus includes a case having a slot unit on one surface thereof; a plurality of slots defined in the slot unit such that a plurality of objects are inserted into and mounted in the plurality of slots; and ultraviolet sources disposed in the respective slots to irradiate ultraviolet on front surfaces and rear surfaces of the objects.

20 Claims, 10 Drawing Sheets

MULTI-CHARGING AND STERILIZING APPARATUS

CROSS REFERENCE TO RELATED APPLICATION

This application claims the benefit of Korean Patent Application No. 10-2013-0131223, filed on Oct. 31, 2013, and Korean Patent Application No. 10-2014-0118851, filed on Sep. 5, 2014, which are hereby incorporated by reference in their entirety into this application.

TECHNICAL FIELD

The present disclosure relates to a multi-charging and sterilizing apparatus, and more particularly, to a multi-charging and sterilizing apparatus capable of simultaneously performing charging and sterilizing for a plurality of objects.

BACKGROUND

As a mobile phone being a mobile communication terminal to transmit voices, text messages or videos over radio waves processes voice calls as well as a variety of information, the mobile phone is regarded as a necessity of a modern person, and the number of users is increasing more and more. The mobile phone includes a microphone for transmitting a user's voice to the inside of the mobile phone. The microphone may be contaminated by saliva produced when a user talks, etc. After contamination has occurred due to saliva, etc., the mobile phone may provide good circumstances for bacteria to propagate, by the heat generated in the course of using the mobile phone. In addition, the mobile phone is always used in contact with the skin while making a call. Also, in the case of a mobile phone having a multimedia function such as a smart phone recently gaining popularity, the mobile phone is used in contact with the skin even while not making a call.

As the mobile phone is regarded as a necessity of a modern person, the mobile phone is highly likely to be contaminated by bacteria. In the case where contaminants on the mobile phone such as bacteria and microorganisms transfer to other items through a user's hand, the mobile phone may serve as a medium that propagates the contaminants to an outside. Further, when making a call using the mobile phone, since the call is made while the ear and the mouth are in contact the mobile phone, the contaminants on the contaminated mobile phone such as bacteria may penetrate into the human body through the user's ear or mouth and may cause various diseases.

Meanwhile, the mobile phone has a rechargeable battery disposed therein. When the rechargeable battery is discharged as a certain time passes or according to a time of using the mobile phone, the rechargeable battery requires charging. Recently, there are growing interests in a multi-charger for simultaneously charging multiple mobile phones, and the introduction of a sterilizing function for the mobile phones charged through such a multi-charger is required.

SUMMARY

Various embodiments are directed to a multi-charging and sterilizing apparatus which has a charging function and a sterilizing function and may allow a sterilizing operation for an object to be performed uniformly on the front surface and the rear surface of the object at the same time with or separately from a charging operation.

In an embodiment, a multi-charging and sterilizing apparatus may include: a case having a slot unit on one surface thereof; a plurality of slots defined in the slot unit such that a plurality of objects are inserted into and mounted in the plurality of slots; and ultraviolet sources disposed in the respective slots to irradiate ultraviolet on front surfaces and rear surfaces of the objects. In an embodiment, the objects may be inserted into and mounted in the plurality of slots in such a way as to be kept inclined.

In an embodiment, the multi-charging and sterilizing apparatus may further include a plurality of charging terminals corresponding to the plurality of slots. The plurality of charging terminals may be disposed at lower ends of the slots.

In an embodiment, a slide dock may be disposed in the case to be moved between a predetermined position in the case and an outside, and a part or an entirety of the plurality of charging terminals may be installed on the slide dock. In a state in which the slide dock is extended to the outside out of the case, at least one of the charging terminals installed on the slide dock may be exposed to the outside. The multi-charging and sterilizing apparatus may further include a stopper interlocked with movement of the slide dock, wherein, when the side dock is extended to the outside out of the case, the stopper may be positioned in a slot in which a corresponding charging terminal is not present. A power supply rail may be formed on any one of the case and the slide dock which are moved relative to each other, and power connection elements which are respectively coupled to the ultraviolet sources disposed in the respective slots may be installed on the other, and connection and disconnection of the power connection elements to and from the power supply rail may be determined according to relative positions of the case and the slide dock.

In an embodiment, guides for guiding the objects to positions of the charging terminals may be disposed in the slots, and the guides may be formed of a material capable of transmitting ultraviolet.

In an embodiment, the charging terminals may be installed on rotation drums which are rotated about respective shafts, and, when the rotation drums are rotated, the objects coupled to the charging terminals may be rotated integrally with rotation of the rotation drums, and the objects may be mounted in the plurality of slots in such a way as to be kept inclined. The rotation drums may be installed on the slide dock. The rotation drums may be movable at least between a first position and a second position, and elastic elements may be installed on the rotation drums to elastically support the rotation drums in a direction for rotating the rotation drums from the second position to the first position. The rotation drums may be movable at least between a first position and a second position, and the rotation drums may include power supply trigger devices which are triggered when the rotation drums are in the second position and supply power to the ultraviolet sources. The multi-charging and sterilizing apparatus may further include ultraviolet reflection plates disposed on both sidewalls of the plurality of slots. In an embodiment, the ultraviolet sources may include ultraviolet light-emitting diodes (UV LEDs).

In an embodiment, the ultraviolet sources may emit ultraviolet with a wavelength of approximately 100 nm to approximately 400 nm.

In an embodiment, the ultraviolet sources may include upper ultraviolet sources which are disposed on upper surfaces of the slots and lower ultraviolet sources which are disposed on lower surfaces of the slots. The upper ultraviolet sources and the lower ultraviolet sources may be disposed in such a way as to face each other in a diagonal direction in the slots.

In an embodiment, the multi-charging and sterilizing apparatus may further include power supply trigger devices triggered when the objects are inserted into and mounted in the slots, and supplying power to the ultraviolet sources.

In an embodiment, the multi-charging and sterilizing apparatus may further include a door capable of being opened and closed to expose and cover the slot unit, wherein the power supply trigger devices corresponding to the respective slots may be connected to the ultraviolet sources which are disposed in the respective slots, and power may be supplied in a state in which the door is closed.

In an embodiment, the ultraviolet sources may be disposed on inner side surfaces of the slots to face side surfaces of the objects in such a way as to be positioned closer to one surfaces of the front surfaces and the rear surfaces of the objects.

In an embodiment, the multi-charging and sterilizing apparatus may further include secondary optics disposed in front of the ultraviolet sources to control divergence angles and beam angles of the ultraviolet sources.

In an embodiment, a multi-charging and sterilizing apparatus may include: a case having a slot unit on one surface thereof; a plurality of slots delimited by delimitation partitions in the slot unit such that a plurality of objects are inserted into and mounted in the plurality of slots; and ultraviolet sources disposed at boundaries of the plurality of slots in the respective slots to irradiate ultraviolet on the objects, wherein ultraviolet sources shared by adjacent slots may irradiate ultraviolet on front surfaces and rear surfaces of the objects.

In an embodiment, the multi-charging and sterilizing apparatus may further include a plurality of charging terminals corresponding to the plurality of slots. The plurality of charging terminals may be disposed at lower ends of the slots.

In an embodiment, the objects may be inserted into and mounted in the slots in such a way as to be kept erected.

In an embodiment, the ultraviolet sources may include ultraviolet light-emitting diodes (UV LEDs).

In an embodiment, the ultraviolet sources may emit ultraviolet with a wavelength of approximately 100 nm to approximately 400 nm.

In an embodiment, the ultraviolet sources may include upper ultraviolet sources which are disposed on upper surfaces of the slots at the boundaries of the slots and lower ultraviolet sources which are disposed on lower surfaces of the slots at the boundaries of the slots.

In an embodiment, the multi-charging and sterilizing apparatus may further include power supply trigger devices triggered when the objects are inserted into and mounted in the slots, and supplying power to the ultraviolet sources.

In an embodiment, the multi-charging and sterilizing apparatus may further include support members supporting the objects in the slots. The support members may include elastic elements which allow widths of the support members to be adjusted according to thicknesses of the objects. The elastic elements may include springs which are installed on both sidewalls of the support members.

DETAILED DESCRIPTION

Figure 1:
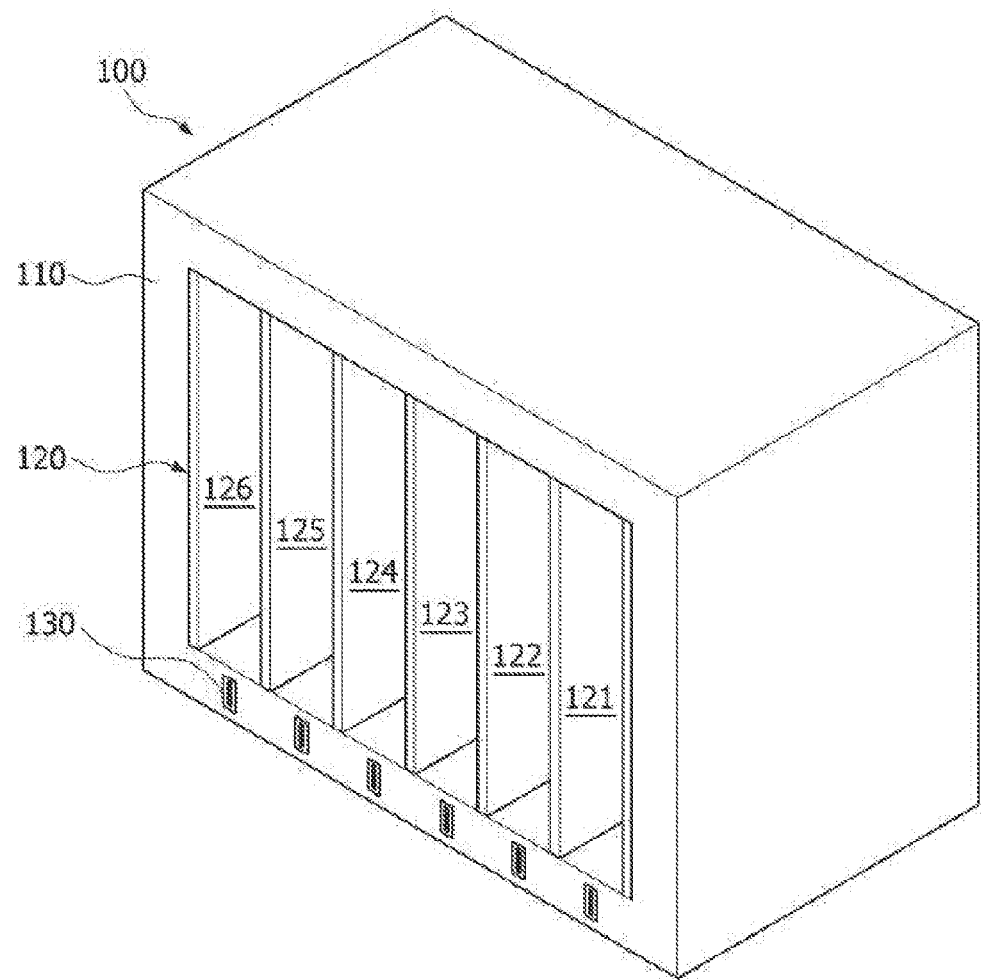
FIG. 1 is a view illustrating a multi-charging and sterilizing apparatus in accordance with an embodiment.

Exemplary embodiments will be described below in more detail with reference to the accompanying drawings. The disclosure may, however, be embodied in different forms and should not be constructed as limited to the embodiments set forth herein. Rather, these embodiments are provided so that this disclosure will be thorough and complete, and will fully convey the scope of the disclosure to those skilled in the art. Throughout the disclosure, like reference numerals refer to like components throughout the various figures and embodiments of the disclosure.

First Embodiment

FIG. 1 is a view illustrating a multi-charging and sterilizing apparatus in accordance with an embodiment. Referring to FIG. 1, a multi-charging and sterilizing apparatus 100 in accordance with an embodiment includes a case 110 which has a slot unit 120 on one surface, for example, the front surface thereof. While the shape in which the slot unit 120 is open toward the front is suggested in the present embodiment, it is to be noted that, as a matter of course, a slot unit may not necessarily face the front and may face the top. Also, while the case 110 has a rectangular box shape in the present embodiment, it is to be noted that, as a matter of course, the case 110 may have a shape other than the rectangular box. Further, while it is shown in the present embodiment that the case 110 provided with the slot unit 120 is always open toward the front, it is to be noted that, as the occasion demands, a door may be installed such that the case 110 may be opened and closed. A plurality of slots 121, 122, 123, 124, 125 and 126 are defined in the slot unit 120. Although it is shown in the drawing that 6 slots 121, 122, 123, 124, 125 and 126 are defined, it is to be noted that the number of slots may be set variously.

A plurality of charging terminals 130 are disposed adjacent to the lower end of the front surface of the case 110. The plurality of respective charging terminals 130 correspond to the respective slots 121, 122, 123, 124, 125 and 126. The charging terminals 130 may be USB ports. The charging terminals 130 may be used for wired charging, or may be used for wireless charging as the occasion demands. Further, while not shown in a drawing, in the case where a charging connection terminal is provided in an object 210 as a target for sterilization, to charge the battery disposed in the object 210, a terminal which may be connected to the charging connection terminal and supply power may be provided in each slot, and as the occasion demands, a guide may be provided in each slot to guide the object 210 such that the connection terminal of the object 210 and the power supply terminal in the slot may be precisely coupled with each other when the object 210 is inserted into the slot. The guide may be manufactured with a material which has a high ultraviolet transmittance such as PMMA with a high monomer ratio.

Figure 2:
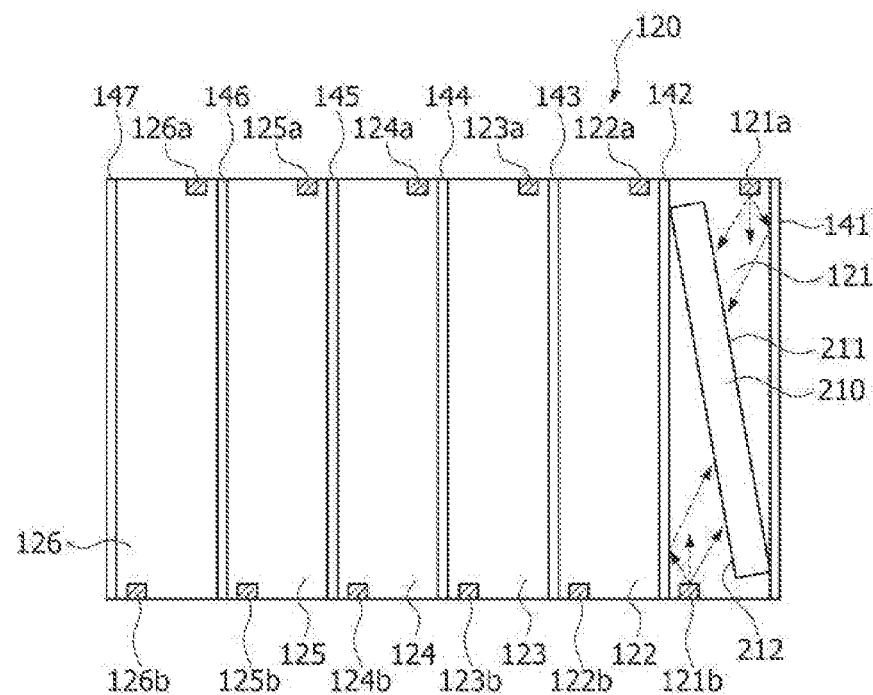
FIG. 2 is a view illustrating the slot unit disposed on the front surface of the multi-charging and sterilizing apparatus shown in FIG. 1.

FIG. 2 is a view illustrating the slot unit 120 disposed on the front surface of the multi-charging and sterilizing apparatus 100 shown in FIG. 1. Referring to FIG. 2, the plurality of slots 121, 122, 123, 124, 125 and 126 are delimited by ultraviolet reflection plates 141, 142, 143, 144, 145, 146 and 147 in the slot unit 120. When performing ultraviolet sterilization within a predetermined space, a sterilizing rate is higher by 2 log or over in the case where ultraviolet reflection plates are installed on walls defining the space than in the case where ultraviolet reflection plates are not installed on walls defining the space. While the plurality of respective slots 121, 122, 123, 124, 125 and 126 have a uniform size, they may have different sizes as the occasion demands. Objects 210 may be respectively inserted into and mounted in the plurality of slots 121, 122, 123, 124, 125 and 126. In the present specification, the objects 210 include not only objects to be charged, for example, portable electronic appliances such as mobile phones, but also objects not to be charged but to be sterilized, for example, books. The objects 120 are respectively mounted in the slots 121, 122, 123, 124, 125 and 126 to be kept inclined therein. According to this fact, one surface 211 of each object 210 is exposed to be inclined toward a right upper part, and an opposite surface 212 of each object 210 is exposed to be inclined toward a left lower part.

Ultraviolet sources 121*a*, 121*b*, 122*a*, 122*b*, 123*a*, 123*b*, 124*a*, 124*b*, 125*a*, 125*b*, 126*a* and 126*b* are disposed in the plurality of respective slots 121, 122, 123, 124, 125 and 126. The ultraviolet sources 121*a*, 121*b*, 122*a*, 122*b*, 123*a*, 123*b*, 124*a*, 124*b*, 125*a*, 125*b*, 126*a* and 126*b* include ultraviolet light-emitting diodes (UV LEDs). The ultraviolet sources 121*a*, 121*b*, 122*a*, 122*b*, 123*a*, 123*b*, 124*a*, 124*b*, 125*a*, 125*b*, 126*a* and 126*b* emit ultraviolet with a wavelength of approximately 100 nm to approximately 400 nm. The ultraviolet sources 121*a*, 121*b*, 122*a*, 122*b*, 123*a*, 123*b*, 124*a*, 124*b*, 125*a*, 125*b*, 126*a* and 126*b* include upper ultraviolet sources 121*a*, 122*a*, 123*a*, 124*a*, 125*a* and 126*a* which are disposed at the top and lower ultraviolet sources 121*b*, 122*b*, 123*b*, 124*b*, 125*b* and 126*b* which are disposed at the bottom. For example, the upper ultraviolet source 121*a* and the lower ultraviolet source 121*b* are respectively disposed at the top and the bottom of the slot 121. In the same manner, the upper ultraviolet source 122*a* and the lower ultraviolet source 122*b* are respectively disposed at the top and the bottom of the slot 122. Upper ultraviolet sources and lower ultraviolet sources are disposed in the remaining slots in the same manner.

The upper ultraviolet sources 121*a*, 122*a*, 123*a*, 124*a*, 125*a* and 126*a* and the lower ultraviolet sources 121*b*, 122*b*, 123*b*, 124*b*, 125*b* and 126*b* are disposed in such a manner that they face each other in a diagonal direction in the respective slots 121, 122, 123, 124, 125 and 126. Therefore, when describing the case of the slot 121 as an example, as shown by the dotted lines in the drawing, the ultraviolet (UV) emitted from the upper ultraviolet source 121*a* is irradiated on the one surface 211 of the object 210, and the ultraviolet (UV) emitted from the lower ultraviolet source 121*b* is irradiated on the opposite surface 212 of the object 210. The ultraviolet (UV) emitted from the upper ultraviolet source 121*a* is uniformly irradiated on the one surface 211 of the object 210 by the ultraviolet reflection plate 141. Similarly, the ultraviolet (UV) emitted from the lower ultraviolet source 121*b* is uniformly irradiated on the opposite surface 212 of the object 210 by the ultraviolet reflection plate 142.

By such a structure in which the objects are kept inclined and the ultraviolet sources are positioned in the diagonal direction opposite to the inclined direction of the objects and irradiate ultraviolet on both surfaces of the objects, sterilization by ultraviolet may be reliably carried out for both surfaces while allowing the slots to be made slim. That is to say, in a structure in which objects are kept erected in slots, because gaps of a predetermined size are needed between both surfaces of each object and two inner walls of each slot which face each other, limitations exist in slimming the slots. In this regard, it is to be readily understood that, in the above-described structure according to the embodiment, it is possible to make slots slim and compact. In the case where ultraviolet light-emitting diodes are used as the ultraviolet sources, secondary optics (such as lenses or light guide panels) may be disposed in front of light emitters to appropriately control the divergence angle and the beam angle of ultraviolet, whereby it is possible to cause ultraviolet to be uniformly and efficiently irradiated on the surfaces of the objects.

Figure 3:
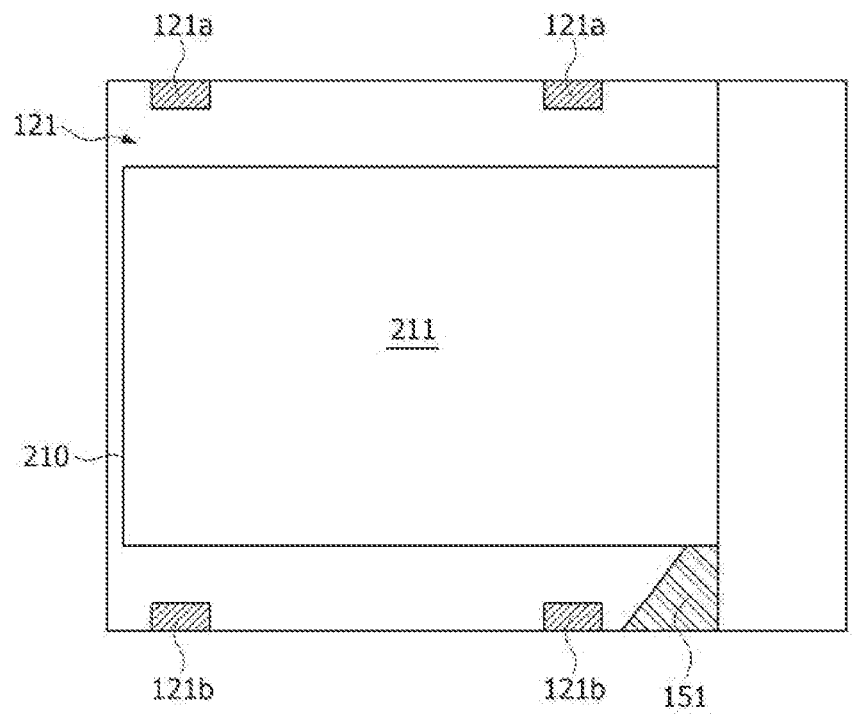
FIG. 3 is a view illustrating the side construction of one slot among slots which form the slot unit of FIG. 2.

FIG. 3 is a view illustrating the side construction of one slot among slots which form the slot unit 120 of FIG. 2. In FIG. 3, the same reference numerals as in FIG. 2 refer to the same components, and accordingly, repeated descriptions will be omitted. Referring to FIG. 3, a power supply trigger device 151 is disposed at the lower end of the slot 121. The power supply trigger device 151 is physically changed as the object 210 is inserted into and mounted in the slot 121, and, by this physical change, transfers a command signal for supplying power to the ultraviolet sources 121*a* and 121*b*, to a power system. If the object 210 is removed, the power supply trigger device 151 is physically recovered, and accordingly, transfers a command signal for interrupting power supply to the ultraviolet sources 121*a* and 121*b*, to the power system. As the occasion demands, the power supply trigger device 151 may perform a timer operation. In other words, when a predetermined time has passed after the power supply trigger device 151 transfers the command signal for supplying power to the ultraviolet sources 121*a* and 121*b*, to the power system, according to a predefined setting value, the power supply trigger device 151 may generate the command signal for automatically interrupting the power supply to the ultraviolet sources 121*a* and 121*b*. Furthermore, in the case where a door is provided as described above to prevent ultraviolet from being exposed to an outside and dust from being introduced into the slots, the power supply trigger device 151 may be enabled by the object 210, and, thereafter, power may be supplied to the ultraviolet sources and ultraviolet may be emitted only when the door is closed.

Second Embodiment

Figure 4:
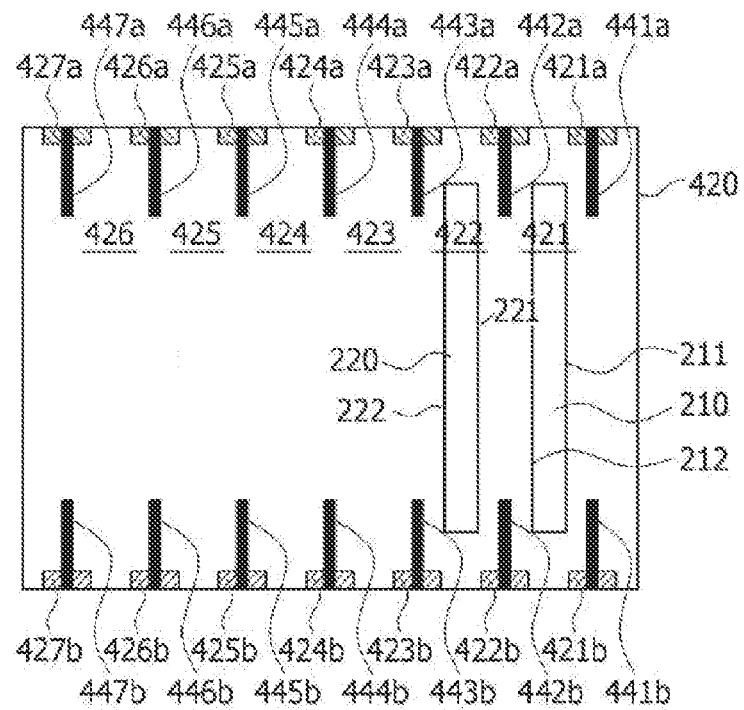
FIG. 4 is a view illustrating the slot unit disposed on the front surface of a multi-charging and sterilizing apparatus in accordance with an embodiment.

FIG. 4 is a view illustrating the slot unit disposed on the front surface of a multi-charging and sterilizing apparatus in accordance with an embodiment. Referring to FIG. 4, a slot unit 420 of the multi-charging and sterilizing apparatus in accordance with the embodiment may be disposed in the same case 110 as in the multi-charging and sterilizing apparatus 100 described above with reference to FIG. 1. A plurality of slots 421, 422, 423, 424, 425 and 426 are delimited in the slot unit 420. The delimitation of the slots 421, 422, 423, 424, 425 and 426 is implemented by upper delimitation partitions 441a, 442a, 443a, 444a, 445a, 446a and 447a and lower delimitation partitions 441b, 442b, 443b, 444b, 445b, 446b and 447b which are respectively disposed at the top and the bottom. The upper delimitation partitions 441a, 442a, 443a, 444a, 445a, 446a and 447a and the lower delimitation partitions 441b, 442b, 443b, 444b, 445b, 446b and 447b are disposed in such a manner that they face each other in a vertical direction at the boundaries of adjacent slots. Objects 210 and 220 may be inserted into and mounted in the plurality of slots 421, 422, 423, 424, 425 and 426. The objects 210 and 220 are inserted into and mounted in the slots 421, 422, 423, 424, 425 and 426 such that they are erected in the slots 421, 422, 423, 424, 425 and 426.

Ultraviolet sources 421a, 421b, 422a, 422b, 423a, 423b, 424a, 424b, 425a, 425b, 426a, 426b, 427a and 427b are disposed at the boundaries of the slots 421, 422, 423, 424, 425 and 426. The ultraviolet sources 421a, 421b, 422a, 422b, 423a, 423b, 424a, 424b, 425a, 425b, 426a, 426b, 427a and 427b include ultraviolet light-emitting diodes (UV LEDs). The ultraviolet sources 421a, 421b, 422a, 422b, 423a, 423b, 424a, 424b, 425a, 425b, 426a, 426b, 427a and 427b emit ultraviolet with a wavelength of approximately 100 nm to approximately 400 nm. The ultraviolet sources 421a, 421b, 422a, 422b, 423a, 423b, 424a, 424b, 425a, 425b, 426a, 426b, 427a and 427b include upper ultraviolet sources 421a, 422a, 423a, 424a, 425a, 426a and 427a which are disposed at the top and lower ultraviolet sources 421b, 422b, 423b, 424b, 425b, 426b and 427b which are disposed at the bottom. For example, the upper ultraviolet source 421a and the lower ultraviolet source 421b are respectively disposed at the right top and the right bottom of the slot 421, and the upper ultraviolet source 422a and the lower ultraviolet source 422b are respectively disposed at the left top and the left bottom of the slot 421. Since the left top and the left bottom of the slot 421 correspond to the right top and the right bottom of the slot 422 adjacent to the slot 421, the upper ultraviolet source 422a and the lower ultraviolet source 422b are shared by the slot 421 and the slot 422 which are adjacent to each other. Upper ultraviolet sources and lower ultraviolet sources are disposed in the remaining slots in the same manner. The upper ultraviolet sources 421a, 422a, 423a, 424a, 425a, 426a and 427a and the lower ultraviolet sources 421b, 422b, 423b, 424b, 425b, 426b and 427b are disposed in such a manner that they face each other in the vertical direction at the boundaries of the slots 421, 422, 423, 424, 425 and 426. Therefore, when describing the case of the slot 421 as an example, the ultraviolet (UV) emitted from the upper ultraviolet source 421a and the lower ultraviolet source 421b is irradiated on one surface 211 of the object 210, and the ultraviolet (UV) emitted from the upper ultraviolet source 422a and the lower ultraviolet source 422b is irradiated on an opposite surface 212 of the object 210. Similarly, in the case of the slot 422, the ultraviolet (UV) emitted from the upper ultraviolet source 422a and the lower ultraviolet source 422b is irradiated on one surface 221 of the object 220, and the ultraviolet (UV) emitted from the upper ultraviolet source 423a and the lower ultraviolet source 423b is irradiated on an opposite surface 222 of the object 220.

Figure 5:
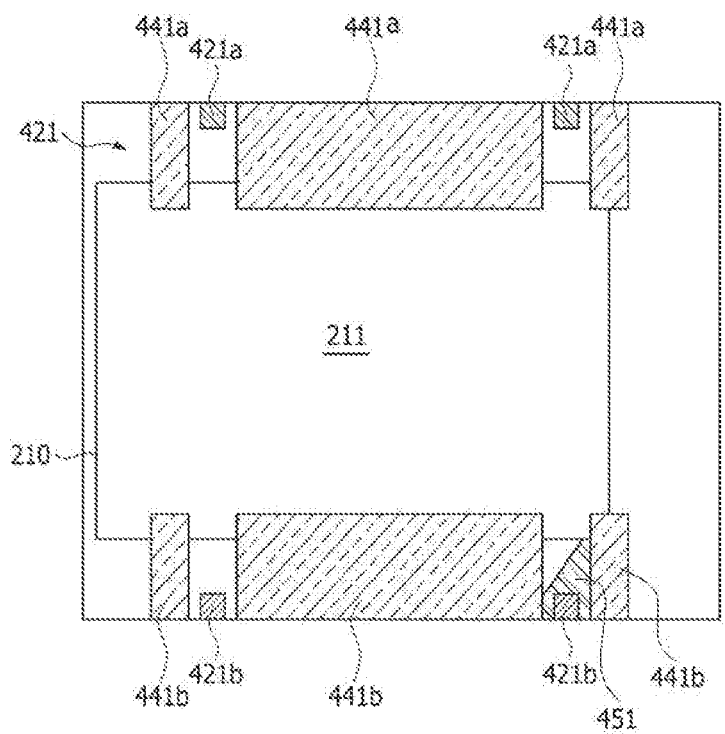
FIG. 5 is a view illustrating the side construction of one slot among slots which form the slot unit of FIG. 4.

FIG. 5 is a view illustrating the side construction of one slot among slots which form the slot unit 420 of FIG. 4. In FIG. 5, the same reference numerals as in FIG. 4 refer to the same components, and accordingly, repeated descriptions will be omitted. Referring to FIG. 5, a power supply trigger device 451 is disposed at the lower end of the slot 421. The power supply trigger device 451 is physically changed as the object 210 is inserted into and mounted in the slot 421, and, by this physical change, transfers a command signal for supplying power to the ultraviolet sources 421a and 421b, to a power system. If the object 210 is removed, the power supply trigger device 451 is physically recovered, and accordingly, transfers a command signal for interrupting power supply to the ultraviolet sources 421a and 421b, to the power system. As the occasion demands, the power supply trigger device 451 may perform a timer operation. Namely, when a predetermined time has passed after the power supply trigger device 451 transfers the command signal for supplying power to the ultraviolet sources 421a and 421b, to the power system, according to a predefined setting value, the power supply trigger device 451 may generate the command signal for automatically interrupting the power supply to the ultraviolet sources 421a and 421b.

Figure 6:
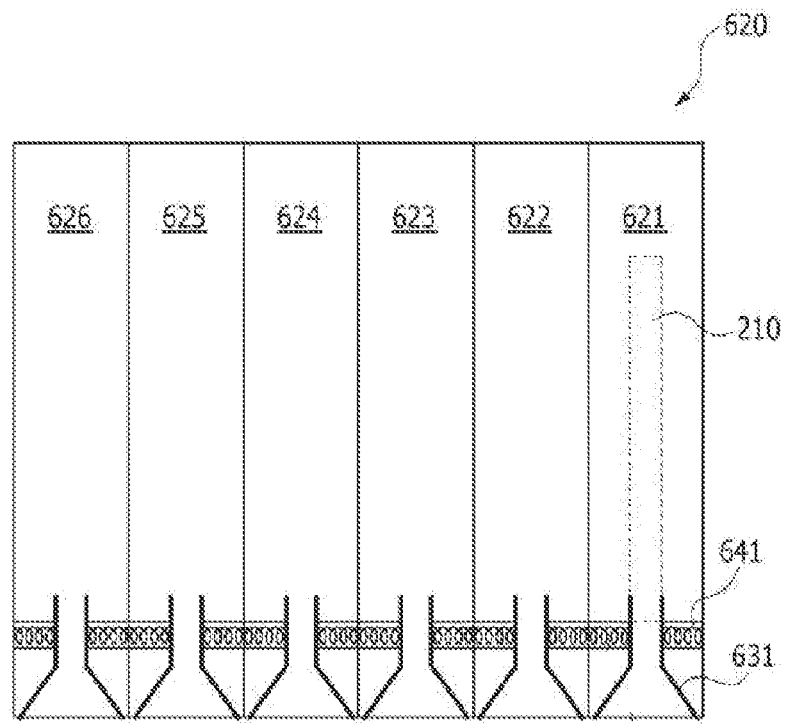
FIG. 6 is a view illustrating the slot unit disposed on the front surface of a multi-charging and sterilizing apparatus in accordance with an embodiment.

FIG. 6 is a view illustrating the slot unit disposed on the front surface of a multi-charging and sterilizing apparatus in accordance with an embodiment. Referring to FIG. 6, a slot unit 620 of the multi-charging and sterilizing apparatus in accordance with the embodiment may be disposed in the same case 110 as in the multi-charging and sterilizing apparatus 100 described above with reference to FIG. 1. A plurality of slots 621, 622, 623, 624, 625 and 626 are defined in the slot unit 620, and, as shown by the dotted lines in the drawing, objects 210 may be inserted into and mounted in the respective slots 621, 622, 623, 624, 625 and 626. In the same manner as described above with reference to FIGS. 4 and 5, ultraviolet sources may be disposed in the slot unit 620. Support members 631 for supporting the objects 210 are disposed at the lower ends of the respective slots 621, 622, 623, 624, 625 and 626. While the height of the support members 631 may be set variously, in any cases, the support members 631 have a height that prevents the objects 210 from bending or inclining. The support members 631 include elastic elements 641 which allow the width of the support members 631 to be adjusted according to the thickness of the objects 210. The elastic elements 641 are installed on both sidewalls of the support members 631. In an embodiment, the elastic elements 641 may be springs.

Third Embodiment

Figure 7:
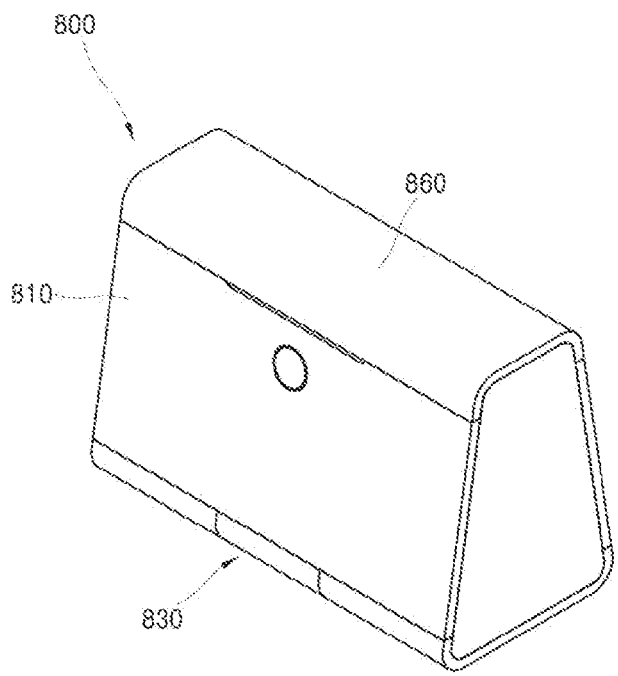
FIG. 7 is a perspective view illustrating a multi-charging and sterilizing apparatus in accordance with an embodiment.
Figure 8:
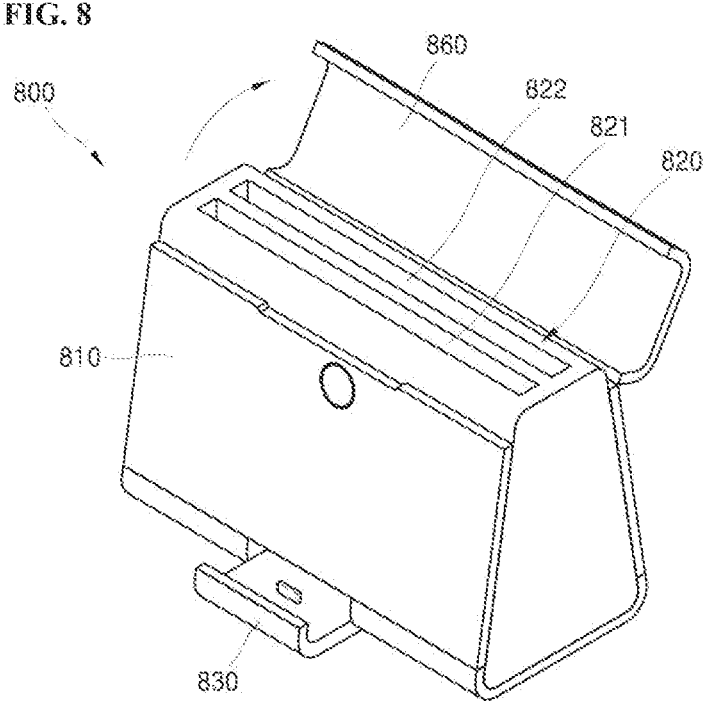
FIG. 8 is a perspective view illustrating a state in which a door is opened and a slide dock is extended forward in the multi-charging and sterilizing apparatus shown in FIG. 7.
Figure 9:
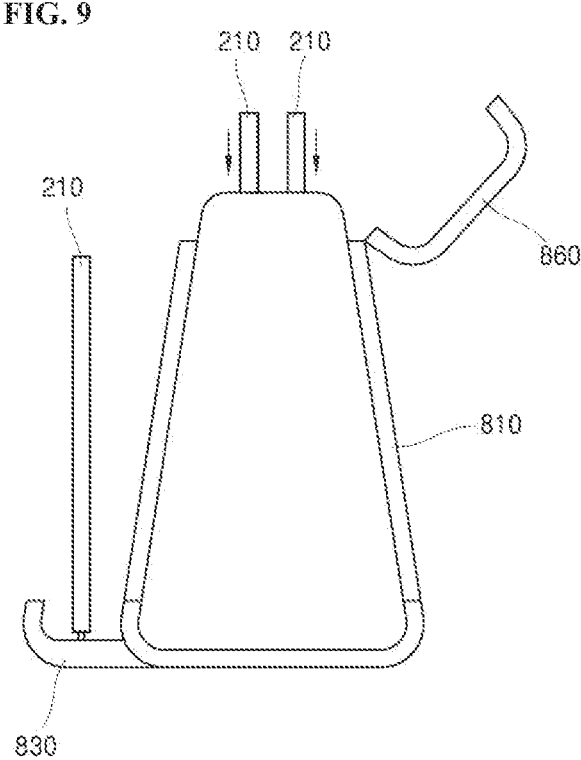
FIG. 9 is a side view illustrating a state in which objects are inserted into the multi-charging and sterilizing apparatus of FIG. 8.
Figure 10:
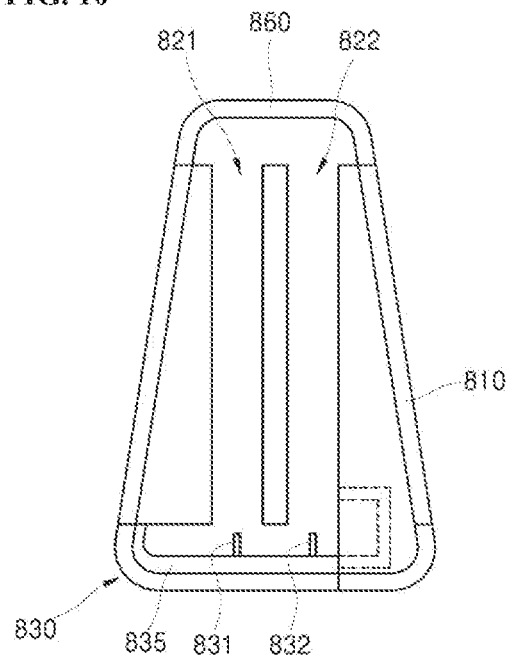
FIG. 10 is a side cross-sectional view of the middle portion of the multi-charging and sterilizing apparatus shown in FIG. 7.
Figure 11:
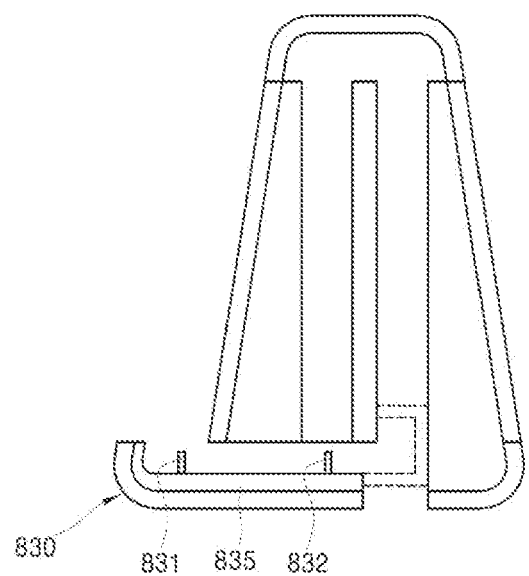
FIG. 11 is a side cross-sectional view illustrating a state in which a slide dock is extended forward in the multi-charging and sterilizing apparatus shown in FIG. 10.
Figure 12:
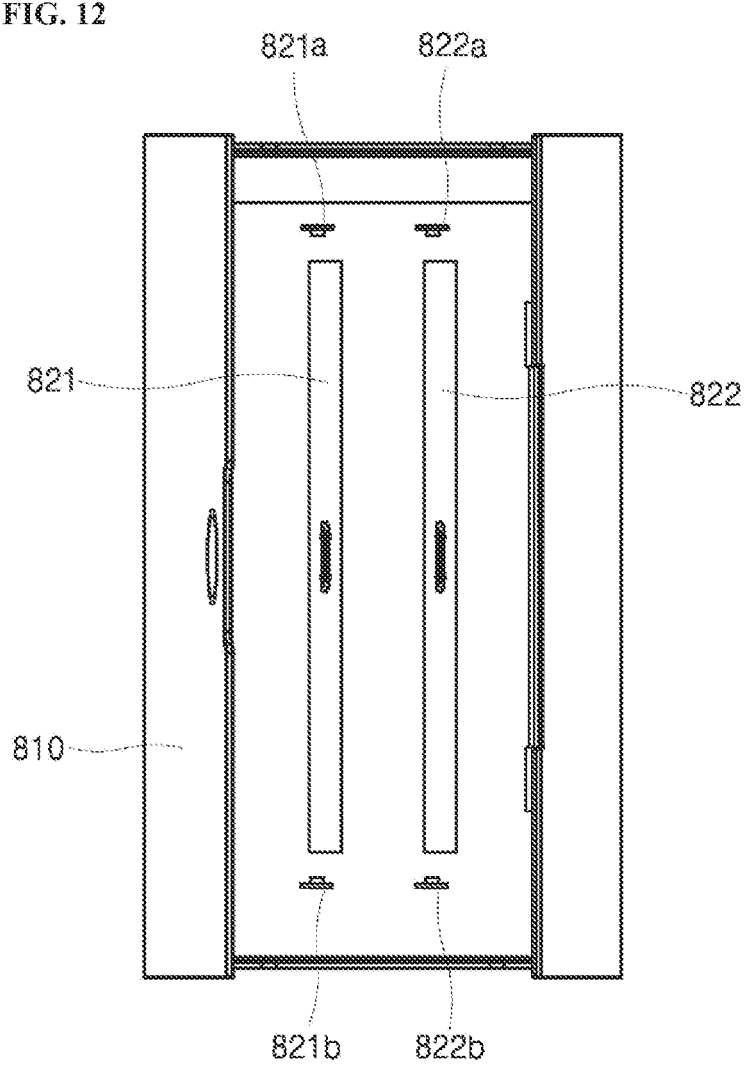
FIG. 12 is a plan view illustrating the insides of slots, with the door of the multi-charging and sterilizing apparatus of FIG. 7 removed.

FIG. 7 is a perspective view illustrating a multi-charging and sterilizing apparatus in accordance with an embodiment, FIG. 8 is a perspective view illustrating a state in which a door is opened and a slide dock is extended forward in the multi-charging and sterilizing apparatus shown in FIG. 7, FIG. 9 is a side view illustrating a state in which objects are inserted into the multi-charging and sterilizing apparatus of FIG. 8, FIG. 10 is a side cross-sectional view of the middle portion of the multi-charging and sterilizing apparatus shown in FIG. 7, FIG. 11 is a side cross-sectional view illustrating a state in which a slide dock is extended forward in the multi-charging and sterilizing apparatus shown in FIG. 10, and FIG. 12 is a plan view illustrating the insides of slots, with the door of the multi-charging and sterilizing apparatus of FIG. 7 removed. Referring to FIGS. 7 to 11, a multi-charging and sterilizing apparatus 800 in accordance with an embodiment includes a case 810, a door 860 which covers the top of the case 810, and a charging terminal 830 which is formed at the lower end of the case 810. The door 860 may be installed to be rotated about the upper end of the rear wall of the case 810 and be turned over rearward. The charging terminal 830 is constructed by a slide dock 835 which may be extended forward out of the case 810 or retracted rearward into the case 810, at the lower end of the case 810.

The case 810 is open at the top thereof, and the open top of the case 810 is exposed when the door 860 is opened. A slot unit 820 is disposed at the top of the case 810 which is open in this way. The slot unit 820 includes a first slot 821 and a second slot 822. That is, the slot unit 820 includes at least two slots. Ultraviolet reflection plates may be installed on the inner side surfaces of the slots 821 and 822. As the case may be, the ultraviolet reflection plates may be used as partitioning plates which delimit the spaces of the slots 821 and 822 (see FIGS. 10 and 11). Of course, partitioning plates may be not necessarily arranged between the slots 821 and 822 (see FIG. 12).

As shown in FIG. 9, a plurality of objects 210 may be mounted in the first slot 821 and the second slot 822 and on the slide dock 835 which is extended forward.

As shown in FIG. 10, the slot unit 820 is accommodated in the case 810, and has a shape which is open at the top thereof. A first charging terminal 831 and a second charging terminal 832, which may be coupled to and decoupled from the charging connection terminals formed in the objects 210, are respectively disposed at the lower ends of the first slot 821 and the second slot 822. Since these charging terminals 831 and 832 are respectively positioned in the middle of the lower ends of the corresponding slots 821 and 822, gaps of a predetermined size are defined between the front and rear surfaces of the objects 210 and the inner walls of the spaces of the slots 821 and 822 in the state in which the objects 210 are coupled to the charging terminals 831 and 832. Although not shown in FIGS. 10 and 11, it will be appreciated that guides, which guide the objects 210 to the charging terminals 831 and 832 and are formed of a material capable of transmitting ultraviolet, may be disposed in the slots 821 and 822.

As shown in FIGS. 10 and 11, the first charging terminal 831 and the second charging terminal 832 are installed on the slide dock 835. As shown in FIG. 10, in the state in which the slide dock 835 is retracted, the first charging terminal 831 and the first slot 821 are aligned with each other, and the second charging terminal 832 and the second slot 822 are aligned with each other. As shown in FIG. 11, in the state in which the slide dock 835 is extended forward, the first charging terminal 831 is exposed in front of the case 810, and the second charging terminal 832 is aligned with the first slot 821.

Power may be always supplied to the first charging terminal 831 and the second charging terminal 832 regardless of whether the slide dock 835 is extended or retracted and whether the door 860 is opened or closed. Therefore, in the state in which the slide dock 835 is retracted as shown in FIG. 10, charging may be carried out by mounting the respective objects 210 in the slots 821 and 822, and, in the state in which the slide dock 835 is extended as shown in FIG. 11, charging may be carried out by mounting the objects 210 on the first charging terminal 831 which is exposed in front of the case 810 and in the first slot 821.

In order to prevent the object 210 from being excessively inserted deep into the second slot 822 defined rearmost and make a user intuitively aware of the non-useable state of the second slot 822 when the slide dock 835 is extended forward, a stopper indicated by the dotted lines in FIGS. 10 and 11 may be caused to be moved integrally with the slide dock 835 or be operated in a manner interlocked with the slide dock 835 as shown in the drawings.

Although not separately shown, unlike the illustration of FIGS. 10 and 11, a slide dock may also be realized in such a manner that the second charging terminal 832 is secured at the position of the second slot 822 and only the first charging terminal 831 is extended forward. Also, unlike this, a third charging terminal may be additionally disposed rearward of the second charging terminal 832 (at the position indicated by the dotted lines in FIGS. 10 and 11), in place of the stopper, in such a manner that the first charging terminal 831 is exposed in front of the case 810 and the second charging terminal 832 and the third charging terminal are respectively aligned with the first slot 821 and the second slot 822 when the slide dock 835 is extended. As another realization example, both the first charging terminal 831 and the second charging terminal 832 may be secured and respectively aligned with the first slot 821 and the second slot 822 and a charging terminal dedicated for the forward extension of the slide dock 835 may be additionally disposed in front of the first charging terminal 831 in such a manner that only the charging terminal dedicated for the forward extension of the slide dock 835 is extended forward along with the slide dock 835 when the slide dock 835 is extended. In addition, when considering that these realization examples are suggested according to the present disclosure, it will be appreciated that various additional modifications may be made by referring to these realization examples.

Moreover, it is of course that the charging terminals may be used for not only wired charging but also wireless charging.

Referring to FIG. 12, a plurality of first ultraviolet sources 821a and 822a and a plurality of second ultraviolet sources 821b and 822b, which respectively emit ultraviolet toward the objects 210, are arranged vertically (in a direction that passes through the plane of the drawing) on both inner side surfaces of the first slot 821 and the second slot 822. The first ultraviolet sources 821a and 822a and the second ultraviolet sources 821b and 822b may be disposed by being deviated slightly forward rather than being positioned in the middle with respect to the side surfaces of the objects 210. This results from the fact that, in the case where each object 210 is an appliance such as a tablet PC or a smart phone of which front surface is in frequent contact with a user's hand, the number of bacterial cells and the contamination degree are larger on the front surface than the rear surface thereof.

While not shown, power supply trigger devices, which may be enabled when the objects 210 are mounted, may be disposed in the first slot 821 and the second slot 822 in such a manner that power may be supplied to only a ultraviolet source disposed in a slot in which the object 210 is mounted, only in the case where the door 860 is closed.

Fourth Embodiment

Figure 13:
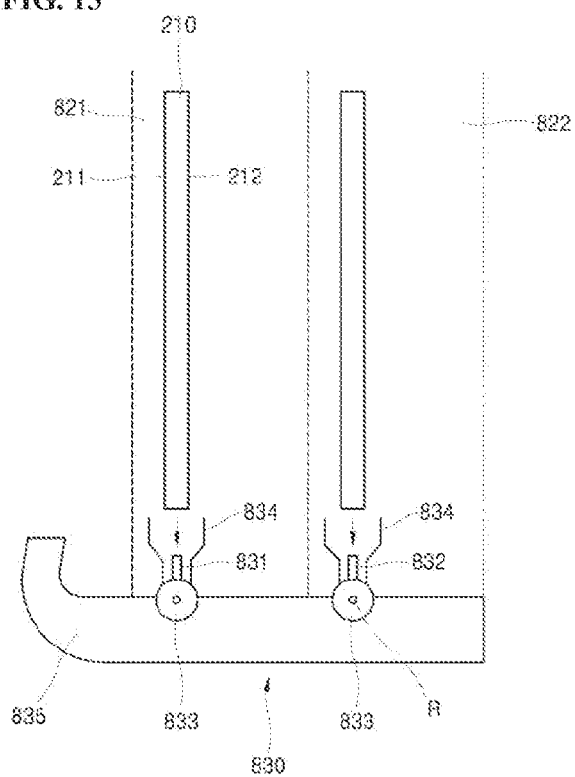
FIGS. 13 and 14 are side views illustrating another realization example of a slide dock.
Figure 14:
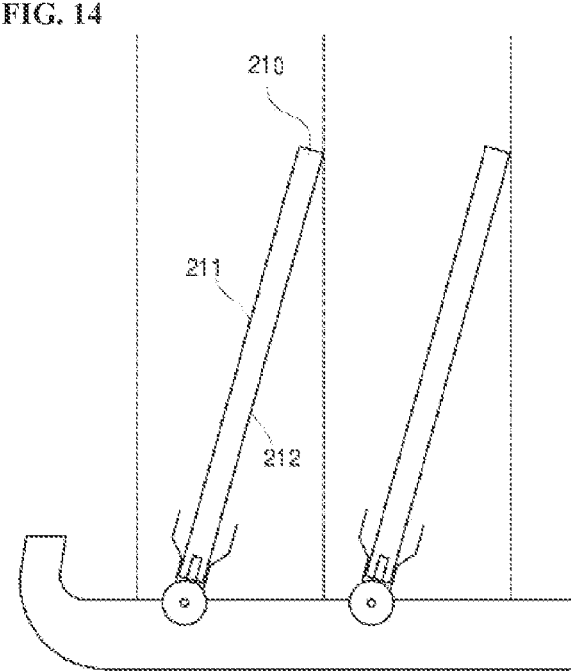
Figure 15:
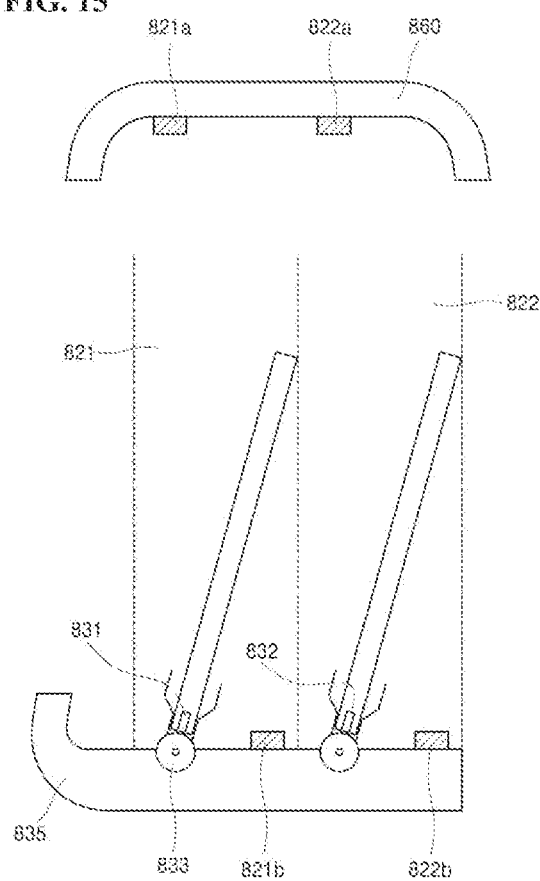
FIGS. 15 and 16 are side cross-sectional views illustrating the disposing positions of ultraviolet sources in the multi-charging and sterilizing apparatus shown in FIG. 7.
Figure 16:
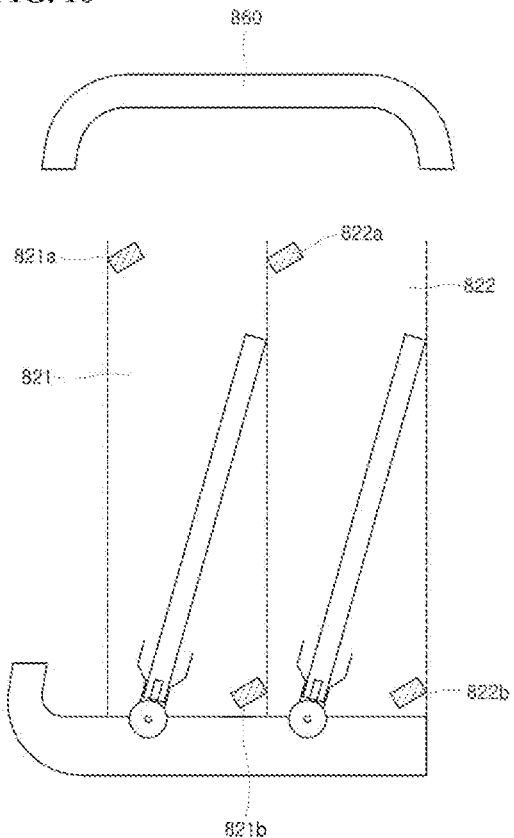
Figure 17:
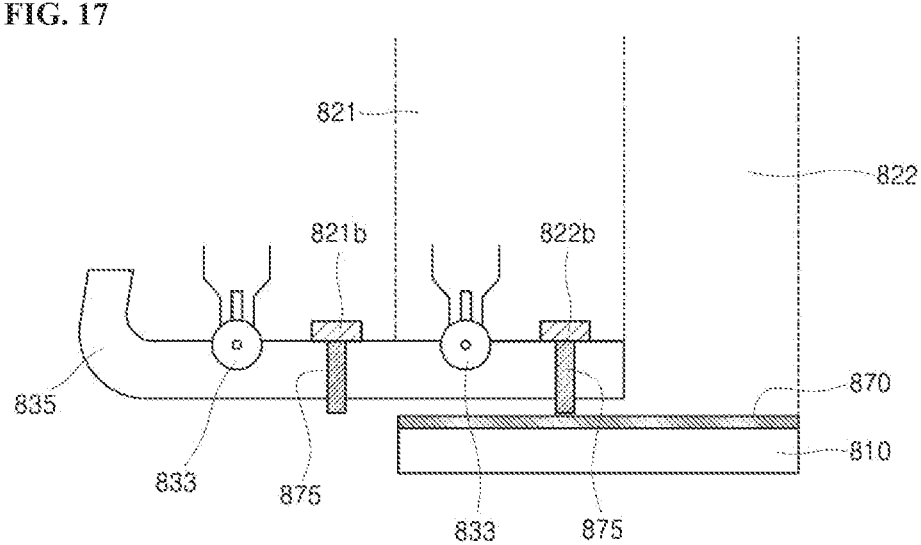
FIG. 17 is a view illustrating a power control structure in accordance with an embodiment.

FIGS. 13 and 14 are side views illustrating another realization example of a slide dock, FIGS. 15 and 16 are side cross-sectional views illustrating the disposing positions of ultraviolet sources in the multi-charging and sterilizing apparatus shown in FIG. 7, and FIG. 17 is a view illustrating a power control structure in accordance with an embodiment. Hereinbelow, descriptions will be made mainly for the differences between FIGS. 13 to 16 and FIGS. 7 to 11.

Both FIGS. 13 and 14 show the state in which the slide dock 835 is retracted. Describing the operating structure of the charging terminals 831 and 832 with reference to FIGS. 13 and 14, the charging terminals 831 and 832 (which may be used for wired charging or wireless charging) are installed on rotation drums 833 which may rotate about shafts R relative to the slide dock 835. Accordingly, if the rotation drums 833 are rotated, the directions of the charging terminals 831 and 832 are also rotated as shown in FIG. 14. The rotation drums 833 may be rotated between positions where the charging terminals 831 and 832 are erected and positions where the charging terminals 831 and 832 are inclined rearward by a predetermined angle. The rotation drums 833 are elastically supported by elastic elements (not shown) in a direction in which the charging terminals 831 and 832 are rotated toward the erected positions. As the occasion demands, dampers may be installed together with the elastic elements such that rotation drums 833 are rotated slowly at a controlled speed when they are rotated by elastic forces. Guides 834, which guide the objects 210 to the charging terminals 831 and 832, are installed on the rotation drums 833.

Therefore, if the user inserts the objects 210 into the slots 821 and 822 and mounts the objects 210 in position under the guidance of the guides 834 as shown in FIG. 13, and then slightly tilts the objects 210, since the centers of gravity of the objects 210 are placed behind the shafts R for rotation, moments are produced. As these moments overcome the elastic forces of the elastic elements, the objects 210 lean rearward along with the rotation drums 833 and are kept inclined as shown in FIG. 14. Conversely, in the case of removing the objects 210, only by slightly moving the objects 210 from the state of FIG. 14, the rotation drums 833 are returned to the original positions of FIG. 13 by the elastic forces of the elastic elements. As a matter of course, it is to be understood that this structure achieves the same effects as those described above with reference to FIG. 2. Besides, in such a structure, in the case where the slide dock 835 is extended forward and the object 210 is mounted to the charging terminal 831 exposed in front of the case 810, it is possible to mount the object 210 in such a way as to be kept inclined against the front surface of the case 810.

In the structure in which the objects 210 are mounted to be kept inclined, as shown in FIGS. 15 and 16, the first ultraviolet sources 821*a* and 822*a* may be installed on the door 860 or adjacent to the upper ends of the front inner walls of the slots 821 and 822, and the second ultraviolet sources 821*b* and 822*b* may be installed on the slide dock 835 or adjacent to the lower ends of the rear inner walls of the slots 821 and 822, in such a manner that, with the objects 210 kept inclined, by positioning the ultraviolet sources 821*a*, 822*a*, 821*b* and 822*b* in a diagonal direction crossing with the inclined direction of the objects 210, ultraviolet may be irradiated on both surfaces of the objects 210.

Power supply trigger devices (not shown) may be installed integrally on the rotation drums 833. Namely, by causing the power supply trigger devices not to operate in the state in which the rotation drums 833 are kept erected as shown in FIG. 13 and to operate in the state in which the rotation drums 833 are rotated rearward by at least a predetermined angle as shown in FIG. 14, powe-r may be supplied to and ultraviolet may be emitted into only a slot in which the rotation drum 833 having the object 210 mounted thereon is rotated rearward. Of course, power may be supplied only when the door 860 is closed.

Meanwhile, although not shown, when the side dock 835 is extended forward such that the first charging terminal 831 is exposed in front of the case 810 and the second charging terminal 832 is aligned with the first slot 821, in the case of the structure in which the ultraviolet sources 821*a*, 822*a*, 821*b* and 822*b* are installed on the door 860 and the slide dock 835 as shown in FIG. 15, it is necessary to cause power not to be supplied to the ultraviolet source 821*b* which is exposed out of the case 810. This may be structurally realized. For instance, as shown in FIG. 17, by installing a power supply rail 870 on the case 810 and individually coupling power connection elements 875 to the respective ultraviolet sources 821*b* and 822*b*, power supply to the ultraviolet source 821*b* exposed to an outside may be structurally interrupted in the case where the slide dock 835 is extended. In addition, it is also possible to control the turn-on timing of the ultraviolet sources 821*a*, 822*a*, 821*b* and 822*b* in terms of circuit by sensing the position of the slide dock 835.

As is apparent from the above descriptions, according to the embodiments, advantages are provided in that a multi-charging and sterilizing apparatus has a charging function and a sterilizing function and may allow a sterilizing operation for an object to be performed uniformly on the front surface and the rear surface of the object at the same time with or separately from a charging operation.

While various embodiments have been described above, it will be understood to those skilled in the art that the embodiments described are by way of example only. Accordingly, the disclosure described herein should not be limited based on the described embodiments.

What is claimed is:

1. A multi-charging and sterilizing apparatus comprising:
 a case having a slot unit on one surface thereof;
 a plurality of slots formed as part of the slot unit and structured to allow for an object to be inserted into and mounted in one of the plurality of slots; and
 ultraviolet sources disposed in the respective slots to irradiate ultraviolet on front surfaces and rear surfaces of the objects.

2. The multi-charging and sterilizing apparatus according to claim 1, wherein the objects are inserted into and mounted in the plurality of slots in such a way as to be kept inclined.

3. The multi-charging and sterilizing apparatus according to claim 1,
 further comprising a plurality of charging terminals corresponding to the plurality of slots,
 wherein a slide dock is disposed in the case to be moved between a predetermined position in the case and an outside, and
 wherein a part or an entirety of the plurality of charging terminals is installed on the slide dock.

4. The multi-charging and sterilizing apparatus according to claim 3, wherein, in a state in which the slide dock is extended to the outside out of the case, at least one of the charging terminals installed on the slide dock is exposed to the outside.

5. The multi-charging and sterilizing apparatus according to claim 3, further comprising:
 a stopper interlocked with movement of the slide dock,
 wherein, when the side dock is extended to the outside out of the case, the stopper is positioned in a slot in which a corresponding charging terminal is not present.

6. The multi-charging and sterilizing apparatus according to claim 3,
 wherein guides for guiding the objects to positions of the charging terminals are disposed in the slots, and
 wherein the guides are formed of a material capable of transmitting ultraviolet.

7. The multi-charging and sterilizing apparatus according to claim 3,
 wherein the charging terminals are installed on rotation drums which are rotated about respective shafts, and
 wherein, when the rotation drums are rotated, the objects coupled to the charging terminals are rotated integrally with rotation of the rotation drums, thus the objects are mounted in the plurality of slots in such a way as to be kept inclined.

8. The multi-charging and sterilizing apparatus according to claim 7,
wherein a slide dock is disposed in the case to be moved between a predetermined position in the case and an outside, and
wherein the rotation drums are installed on the slide dock.

9. The multi-charging and sterilizing apparatus according to claim 7,
wherein the rotation drums are movable at least between a first position and a second position, and
wherein elastic elements are installed on the rotation drums to elastically support the rotation drums in a direction for rotating the rotation drums from the second position to the first position.

10. The multi-charging and sterilizing apparatus according to claim 7,
wherein the rotation drums are movable at least between a first position and a second position, and
wherein the rotation drums include power supply trigger devices which are triggered and supply power to the ultraviolet sources when the rotation drums are in the second position.

11. The multi-charging and sterilizing apparatus according to claim 1, wherein the ultraviolet sources comprise upper ultraviolet sources which are disposed on upper surfaces of the slots and lower ultraviolet sources which are disposed on lower surfaces of the slots,
wherein the upper ultraviolet sources and the lower ultraviolet sources are disposed in such a way as to face each other in a diagonal direction in the slots.

12. The multi-charging and sterilizing apparatus according to claim 1, further comprising:
power supply trigger devices triggered and supplying power to the ultraviolet sources when the objects are inserted into and mounted in the slots.

13. The multi-charging and sterilizing apparatus according to claim 12, further comprising:
a door capable of being opened and closed to expose and cover the slot unit,
wherein power is supplied only to the ultraviolet sources in the slots in which the power supply trigger device is triggered in a state in which the door is closed.

14. The multi-charging and sterilizing apparatus according to claim 1, wherein the ultraviolet sources are disposed on inner side surfaces of the slots to face side surfaces of the objects in such a way as to be positioned closer to one surfaces of the front surfaces and the rear surfaces of the objects.

15. A multi-charging and sterilizing apparatus comprising:
a case having a slot unit on one surface thereof, wherein the slot unit includes delimitation partitions to form a plurality of slots structured to allow a plurality of objects to be inserted into and mounted in the plurality of slots, respectively; and
ultraviolet sources disposed at boundaries of the plurality of slots in the respective slots to irradiate ultraviolet on the objects,
wherein ultraviolet sources shared by adjacent slots irradiate ultraviolet on front surfaces and rear surfaces of the objects.

16. The multi-charging and sterilizing apparatus according to claim 15, wherein the ultraviolet sources comprise upper ultraviolet sources which are disposed on upper surfaces of the slots at the boundaries of the slots and lower ultraviolet sources which are disposed on lower surfaces of the slots at the boundaries of the slots.

17. The multi-charging and sterilizing apparatus according to claim 15, further comprising:
power supply trigger devices triggered when the objects are inserted into and mounted in the slots, and supplying power to the ultraviolet sources.

18. The multi-charging and sterilizing apparatus according to claim 15, further comprising:
support members supporting the objects in the slots.

19. The multi-charging and sterilizing apparatus according to claim 18, wherein the support members comprise elastic elements which allow widths of the support members to be adjusted according to thicknesses of the objects.

20. The multi-charging and sterilizing apparatus according to claim 19, wherein the elastic elements comprise springs which are installed on both sidewalls of the support members.

* * * * *